United States Patent [19]

Oriel et al.

[11] Patent Number: 5,688,673
[45] Date of Patent: *Nov. 18, 1997

[54] PROCESS FOR THE PREPARATION OF MONOTERPENES USING BACTERIUM CONTAINING RECOMBINANT DNA

[75] Inventors: Patrick J. Oriel, Midland; Srinivasan Savithiry, East Lansing, both of Mich.; Hae Choon Chang, Taejeon, Rep. of Korea

[73] Assignee: Board of Trustees operating Michigan State University, East Lansing, Mich.

[*] Notice: The term of this patent shall not extend beyond the expiration date of Pat. No. 5,487,988.

[21] Appl. No.: 508,818

[22] Filed: Jul. 28, 1995

Related U.S. Application Data

[63] Continuation-in-part of Ser. No. 290,469, Aug. 15, 1994, Pat. No. 5,487,988.
[51] Int. Cl.[6] .................. C12P 7/24; C12P 7/02; C12N 1/21; C12N 15/70
[52] U.S. Cl. .................. 435/147; 435/155; 435/252.33; 435/252.5; 435/320.1
[58] Field of Search .................. 435/147, 320.1, 435/155, 252.5, 832, 252.33

[56] References Cited

U.S. PATENT DOCUMENTS

| | | | |
|---|---|---|---|
| 4,495,284 | 1/1985 | Rhodes et al. | 435/148 |
| 5,110,832 | 5/1992 | Chadstain et al. | 514/729 |
| 5,487,988 | 1/1996 | Chang et al. | 435/147 |

OTHER PUBLICATIONS

Alonso et al. "Production & Characterization of Polyclonal Antibodies in Rabbits to 45–Limorene Synthae from Spearmint" Act Biochem Biophys 301(1) 58–63 1993.

Kieslich et al., Transformation of terpenoids. in Progress in essential oil research. XVI. Ernst–Joachin Brunke (Ed.) . 372 –394 (1986).

Braddock and Cadwallader, Food Technol. 40 (2) : 105–110 (1992).

Krasnobajew, V. Terpenoids Ch. 4. In "Biotechnology–Biotransformations" vol 6a. K. Lieslich (Ed.) . 104–109. Verlag Chemie, Weinheim (1984).

Cadwallader et al., J. Food Sci. 54:1241–1245 (1989).

Dhavlikar et al., Indian J. Biochem. 3:144–157 (1966).

Dhavalikar et al., Indian J. Biochem. 3:158–164 (1966).

Uribe and Pena, J. Chem. Ecol. 16:1399–1408 (1990).

Dower, W. J., et al., Nucleic Acids Res. 16:6127–61 39 (1988).

Chang, H.C., et al., Journal of Food Science 60 551–553 (1995).

Maniatis, T., et al., Molecular cloning: a laboratory manual. 2nd ed. Cold Spring Harbor Laboratory, Cold Spring Harbo, N.Y. (1989).

Chang, H. C. and P. Oriel, J. Food Sci. 59:660–662 (1994) p. 440; 368–389.

*Primary Examiner*—Nancy Degen
*Attorney, Agent, or Firm*—Ian C. McLeod

[57] ABSTRACT

A process for producing monoterpenes using a DNA segment *Bacillus stearothermophilus* in a recombinant bacterium, particularly *Escherichia coli*. The useful monoterpenes produced from limonene are perillyl alcohol, perillyl aldehyde, perillic acid (path A); alpha-terpineol (path B) or carveol and carvone (path C).

36 Claims, 2 Drawing Sheets

PROCESS FOR THE PREPARATION OF MONOTERPENES USING BACTERIUM CONTAINING RECOMBINANT DNA

CROSS-REFERENCE TO RELATED APPLICATION

This application is a continuation-in-part of U.S. Ser. No. 08/290,469, filed Aug. 15, 1994, now U.S. Pat. No. 5,487,988.

BACKGROUND OF THE INVENTION

1. Field of the Invention

The present invention relates to a process for the preparation of monoterpenes using a novel bacterium containing recombinant DNA. In particular the present invention relates to *Escherichia coli* containing a segment which is 9.6 kb in length which is an EcoR1 digest of the DNA of a *Bacillus stearothermophilus* or containing a subfragment of the 9.6 kb segment which is a 3.9 kb endonuclease HindIII segment of the 9.6 kb segment and their use to produce monoterpenes.

2. Description of Related Art

The monocyclic terpenoid (+) limonene ((R)1-cyclohexen-1-methyl 4-(1-methylethyl)) is an attractive monoterpene starting compound for microbial bioconversion to higher value monoterpenes utilized in flavor and perfume applications (Kieslich et al., Transformation of terpenoids. in Progress in essential oil research. XVI. Ernst-Joachin Brunke (Ed.). 372–394 (1986)). (+) Limonene is a common constituent of many essential oils and is the major component in oils derived from citrus product waste peels (Braddock and Cadwallader, Food Technol. 40(2):105–110 (1992)). As a result, it is one of the least expensive and widely available terpenes, and is used directly in a number of food and other applications (Krasnobajew, V., Terpenoids Ch. 4. In "Biotechnology-Biotransformations" Vol 6a. K. Lieslich (Ed.). 104–109. Verlag Chemie, Weinheim (1984)). Useful oxidation products of (+) limonene include perillyl alcohol ((R) 1-cyclohexene-1-methanol-4-(1-methylethyl)); perillyl aldehyde ((R)1-cyclohexene-1-carboxaldehyde 4-(1-methylethyl)), and perillic acid ((R)1-cyclohexene-1-carboxylic acid-4-(1-methylethyl)). These are naturally found in low quantities in citrus, lemon grass, and perilla oils, and are utilized as flavorings and as antimicrobial agents in foods and pharmaceuticals.

The possibility of microbial conversion of limonene to other monoterpenes of interest has been examined, and bacteria have been isolated which are capable of growth on limonene to yield metabolites such as (+)-α-terpineol, (+)-limonene-1,2-diol, (+)-perillic acid, (+)-β-isopropenyl pimelic acid, carveol, perillyl alcohol and perillyl aldehyde (Braddock and Cadwallader, Food Technol. 40:105–110 (1992); (Cadwallader et al, J. Food Sci. 54:1241–1245 (1989); Dhavlikar et al, Indian J. Biochem. 3:144–157 (1966); and Krasnobajew, V., Terpenoids Ch. 4. In "Biotechnology-Biotransformations" Vol 6a. K. Lieslich (Ed.). 104–109. Verlag chemie, Weinheim (1984) Kieslich, K., et al., Transformation of terpenoids. in progress in essential oil research. XVI. Ernst-Joachin Brunke (Ed.) 367–394 (1986)). While these findings are of scientific interest, commercialization of these processes has been thwarted by the multiplicity of conversion products produced, and the low conversion product concentrations which has been found to be due to the toxicity of limonene to most microorganisms (see Dhavalikar et al, Indian J. Biochem. 3:158–164 (1966); Uribe and Pena, J. Chem. Ecol. 16:1399–1408 (1990); and Chadstain, D. E., et al., U.S. Pat. No. 5,110,832).

U.S. Pat. No. 5,110,832 to Chadstain et al shows that bacteria, particularly *Bacillus* are killed by perillyl alcohol. The compound α-terpineol is also inhibitory to microorganisms. Thus, there is a problem in finding bacteria which produce such metabolites.

OBJECTS

It is therefore an object of the present invention to provide a process using novel bacteria containing recombinant DNA which are uniquely adapted to producing monoterpenes in significant yield, particularly from limonene. Further, it is an object to provide novel DNA and plasmids for the novel bacteria. Further still, it is an object of the present invention to provide a process using the novel bacteria for the production of monoterpenes which is relatively simple and economical. These and other objects will become increasingly apparent by reference to the following description and the drawings.

DESCRIPTION OF PREFERRED EMBODIMENTS

Figure 1:
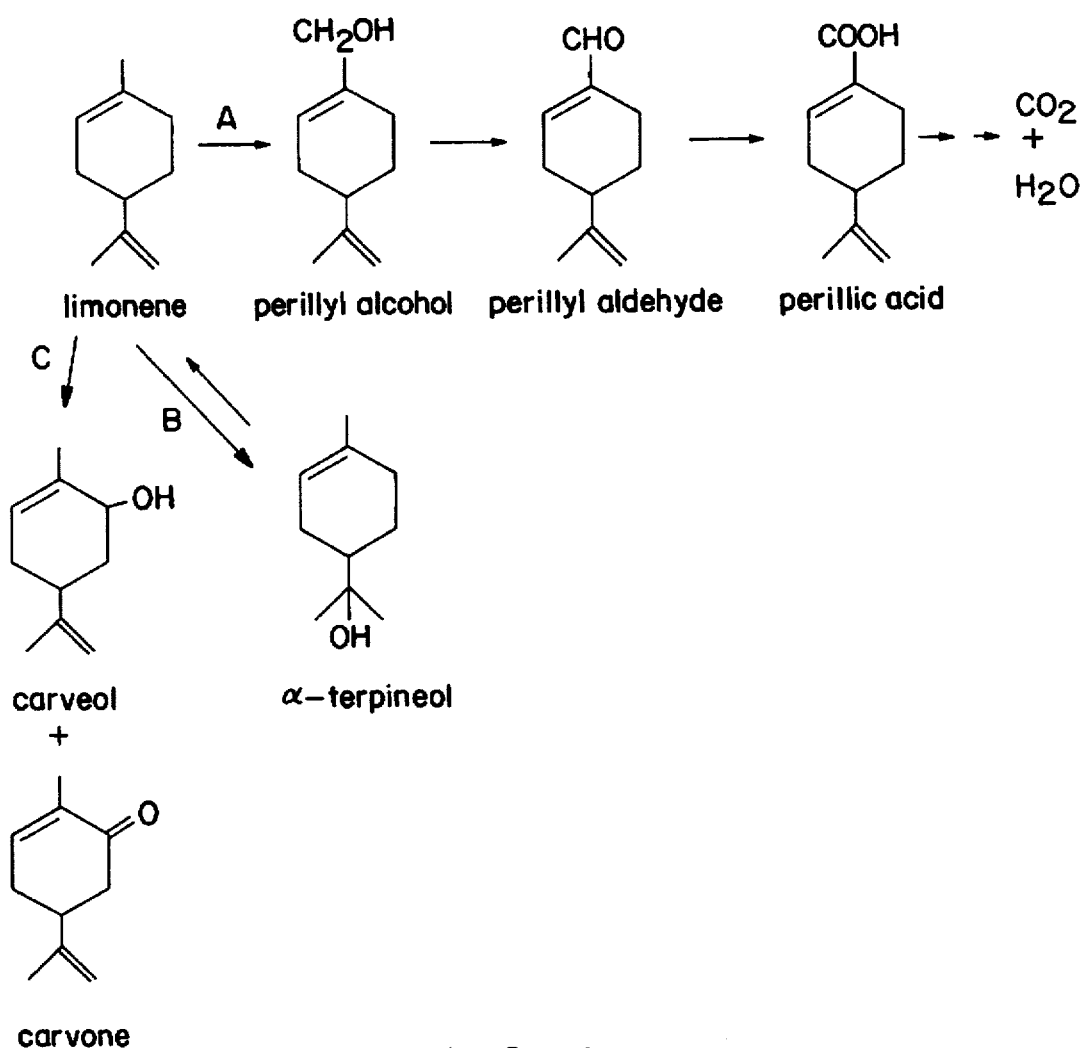
FIG. 1 is a diagram showing deduced degradation pathways for *Bacillus stearothermophilus* BR219A and *Escherichia coli* EC409A from limonene as the monoterpene. A denotes a deduced main pathway for limonene catabolism. B denotes limonene conversion to dead end metabolite, α-terpineol. C denotes conversion to carveol and carone.

The present invention relates to a recombinant plasmid containing a segment of DNA of a *Bacillus stearothermophilus* which converts limonene to a monoterpene compound in a culture medium.

In particular, the present invention relates to a recombinant plasmid containing a segment of DNA from *Bacillus stearothermophilus* which converts limonene to carveol.

Further, the present invention relates to an *Escherichia coli* containing a segment of DNA of *Bacillus stearothermophilus* which converts limonene to a monoterpene compound in a culture medium.

In particularly the present invention relates to an *Escherichia coli* containing a segment of DNA from *Bacillus stearothermophilus* which converts limonene to carveol and carvone.

Further, the present invention relates to a process for producing monoterpene compounds which comprises: providing a culture medium containing cells of *Escherichia coli* containing a segment of DNA of *Bacillus stearothermophi-*

*lus* which converts limonene to a monoterpene compound; and incubating the cells in the culture medium in the presence of the limonene to produce isolatable amounts of the monoterpene compound in the culture medium.

Further still, the present invention relates to a process for the production of carveol which comprises: providing a culture medium containing cells of *Escherichia coli* containing a segment of DNA of *Bacillus stearothermophilus* which converts limonene to carveol and carvone in the culture medium.

The present invention also relates to an isolated and purified segment of DNA which is 9.6 kb segment of endonuclease EcoRI digest of DNA of *Bacillus stearothermophilus* deposited as ATCC 55596.

Finally, the present invention relates to an isolated and purified segment of DNA which is a 3.8 kb endonuclease HindIII digest of a 9.6 kb segment endonuclease EcoRI digest of DNA of *Bacillus stearothermophilus* deposited as ATCC 55596.

The DNA used in the present invention is from a *Bacillus stearothermophilus* (BR388) isolated from a citrus skin, particularly peel or skin. The most preferred strain is *Bacillus stearothermophilus* deposited under the Budapest Treaty with the American Type Culture Collection, Rockville, Md. as ATCC 55596 and as described in detail in Ser. No. 08/290,469, now U.S. Pat. No. 5,487,988, filed Aug. 15, 1994. The strain is available upon request by name and deposit number.

*Bacillus stearothermophilus* ATCC 55596 (BR388) was isolated from orange peel by an enrichment culture using (+)-limonene vapor. The thermophilic isolate exhibited growth between 45° and 68° C., with an optimum growth temperature near 55° C. BR388 could grow on limonene as a sole carbon source, but grew and degraded limonene more effectively when supplemented with low amounts of yeast extract. Perillyl alcohol was identified as the major conversion product, with α-terpineol and perillyl aldehyde formed as minor products. Other strains of *Bacillus stearothermophilus* previously isolated from aromatic enrichments were also shown able to grow on limonene, but demonstrated higher toxicity by limonene than BR388 which is preferred.

Preferably the culture medium for *Bacillus stearothermophilus* or *E. coli* contains yeast extract or another protein and amino acid source which is assimilable by the *Bacillus stearothermophilus*. The remainder of the culture medium is one which is standard for growing *Bacillus* or *E. coli* and are available from numerous sources, such as Difco, Detroit, Mich. The culture medium is preferably incubated at a temperature between about 30° and 60° C. with the recombinant *E. coli*.

The limonene or other monoterpene is preferably provided in the culture medium as a vapor so that the recombinant *E. coli* cells are not inhibited. The monoterpene can also be added in small increments over time directly to the culture medium. All of these means of providing the limonene in the culture medium are well known to those skilled in the art.

The monoterpene compounds formed are separated from the culture medium. This is easily accomplished by organic solvent extraction, preferably using diethyl ether. The individual compounds can be separated using liquid chromatography (such as HPLC) or other means known to the art.

As shown in U.S. application Ser. No. 08/290,469, now U.S. Pat. No. 5,487,988, thermostable enzymes of *Bacillus stearothermophilus* provide resistance to chemical inactivation by limonene. The *Bacillus stearothermophilus* thermophile (BR388) is capable of limonene degradation with production of α-terpineol and perillyl alcohol. Microbial catabolic pathways have not been elucidated for monoterpenes in either mesophilic or thermophilic microorganisms. DNA from the stearothermophilus is cloned into *E. coli* in the present invention to produce a recombinant *E. coli* capable of converting monoterpenes. Cloning of the limonene pathway into *E. coli* allows a better understanding of the enzymes participating in monoterpene catabolism and the biochemical origin of observed metabolites in the hope of controlling their formation in biotechnological applications.

The pathway encoding limonene catabolism was cloned as a 9.6 kb chromosomal endonuclease EcoRI digest fragment from *Bacillus stearothermophilus* strain BR388 into *Escherichia coli*, conferring growth on limonene as a sole carbon source with bioproduction of α-terpineol, perillyl alcohol, and perillyl aldehyde. Incubation of the recombinant *Escherichia coli* with perillyl alcohol resulted in formation of perillyl aldehyde and perillic acid. The deduced catabolic pathways are pathways A and B as shown in FIG. 1. A 3.9 kb HindIII digest of the 9.6 kb fragment produced DNA which is *Escherichia coli* converted limonene to carveol and carvone as shown as pathway C.

EXAMPLE 1

Thus Example 1 shows the cloning of a 9.6 kb segment of the chromosomal DNA of *Bacillus stearothermophilus* into a plasmid vector which is transformed into *Escherichia coli*. The recombinant *Escherichia coli* produced terpenes from limonene. The recombinant *Escherichia coli* is deposited as ATCC 69817 under the Budapest Treaty with the American Type Culture Collection, Rockville, Md. and is available upon request by name and number of the bacterium.

MATERIALS AND METHODS

Bacterial strains, plasmids, media and reagents *Bacillus stearothermophilus* BR388 (ATCC 55596), whose isolation and maintenance was described in U.S. Ser. No. 290,469, was grown and maintained on DP minimal medium (per liter: $NH_4Cl$, 1.0 g; $K_2HPO_4$, 0.5 g; $MgSO_4 \cdot 7H_2O$, 20 mg pH 7.2) with limonene vapor or LB medium (per liter: Bacto-tryptone, 10 g; yeast extract, 5 g; NaCl 5 g) at 55° C. *Escherichia coli* XL-1 [recA-(recA1, lac-, endA1, gyrA96, thi, hsdR17, supE44, relA1, ($F^1$ proAB, lacIq, lacZDM15, Tn10))), used for construction and maintenance of plasmids, was cultured at 37° C. on LB medium. When appropriate, the medium was supplemented with ampicillin (50 µg/ml), tetracycline (12.5 µg/ml) and 5-bromo-4-chloro-3-indolyl-β-galactoside (40 µg/ml). pBluescriptII SK⁻ (Stratagene, Lajolla, Calif.) was used as a cloning vector. Plasmids were introduced into *E. coli* by electroporation at 200 volts (Dower, W. J., et al., Nucleic Acids Res., 16:6127–6127 (1988)). The monoterpenes (+) limonene, (+) perillic acid, and α-terpineol were obtained from Aldrich Co. (+) perillyl alcohol and (+) perillyl aldehyde were purchased from Nippon Terpene Chemical Co., Japan.

DNA procedures. Plasmid DNA was isolated from *E. coli* by the alkaline lysis method. Total DNA of *Bacillus stearothermophilus* BR388 was prepared by the method of Saito and Miura (Saito, H., and K. I. Miura., Biochim. Biophys. Acta. 72:619–629 (1963)). DNA fragments were isolated from agarose gels by using electroelution (IBI, New Haven, Conn.). Southern hybridization was performed as described by Maniatis et al (Maniatis, T., et al., Molecular cloning: a laboratory manual. 2nd ed. Cold Spring Harbor Laboratory, Cold Spring Harbor, N.Y. (1989)). Restriction enzymes, DNA ligase, and alkaline phosphatase were purchased from Boehringer Mannheim Co. (Indianapolis, Ind.). For hybridization studies, DNA was labeled by random-primed incorporation of digoxigenin (DIG)-labeled deoxyuridine-triphosphate (dUTP) and detected using a DIG DNA labeling and detection kit, (Boehringer Mannheim Co., Indianapolis,Ind.). Hybridization was carried out using conditions recommended by the manufacturer.

Screening for transformants capable of limonene growth. Transformants were spread on M9 salt agar media (available from Difco, Detroit, Mich.) with 50 μg/ml of ampicillin and 40 μg/ml of X-gal containing 100 ml of limonene in a small glass tube attached to the cover to provide a vapor, and incubated at 37° C. Culture demonstrating growth on repeated transfer were selected for further examination.

Growth and biotransformation studies. Triple-baffled 250 ml culture flasks with a sidearm (Bellco Glass Inc., Vineland, N.J.) were used for microbial growth and biotransformation studies. These flasks allowed vapor introduction of (+) limonene, (+) perillyl alcohol, or α-terpineol into the culture from perpene contained in the sidearm.

For perillyl alcohol biotransformation studies, a 1% inoculum of cells grown in M9 medium on limonene vapor was introduced into 75 ml M9 salts medium with 0.006% yeast extract and perillyl alcohol contained in the sidearm of a 250 ml closed culture flask. After 36 hours incubation with shaking at 37° C., cells were removed by centrifugation and terpene products analyzed.

Product Extraction and Analysis. After cell removal by centrifugation, the culture supernatant was separated into acidic and neutral fractions and extracted with ether as previously described (Chang, H. C. and P. Oriel, J. Food Sci. 59:660–662 (1994)). The GC-MS system utilized was a HP5970 mass spectrometer coupled with a HP5980 gas chromatography (Hewlett Packard, Farmington, N.Y.). The mass detector was an MSD HP5970 (Hewlett Packard, Farmington, N.Y.). A 0.25 mm ID×30 m DB-wax fused silica capillary column (J & W Scientific Co., Folson, Calif.) was used for separation. running conditions were 1 μl injection; He carrier gas; injection port and detector port at 240° C.; column temperature programmed from 40°–240° C. at 7° C./min with a 2 min initial hold time.

RESULTS

Figure 2:
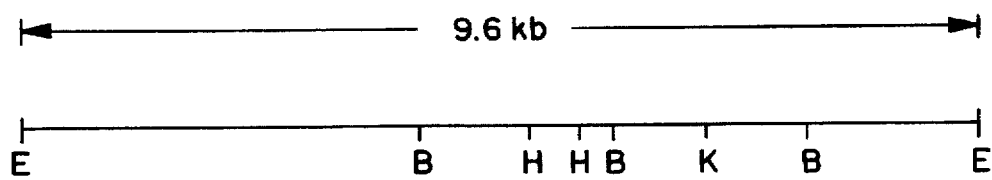
FIG. 2 is a partial restriction map of a 9.6 kb plasmid insert in *Escherichia coli* EC409A. Abbreviations: E, EcoRI; B, BamHI; H, HindIII; K, KpnI. No cleavage sites were detected within the insert for restriction enzymes ClaI, PstI, SalI, and XbaI.
Figure 3:
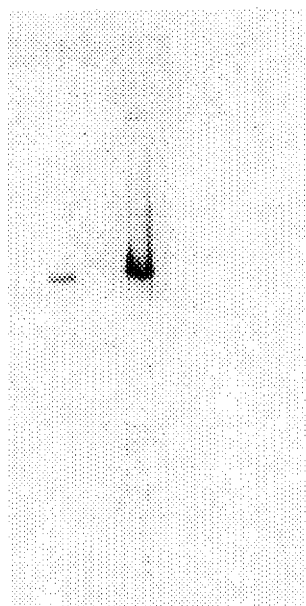
FIG. 3 is a film of a southern blot showing hybridization with the *Escherichia coli* EC409A cloned insert. Molecular weight marker positions are noted. Lane 1:EcoRI digest of *Bacillus stearothermophilus* BR219 DNA. Lane 2, EcoRI digest of a recombinant plasmid of EC409A.

Cloning of the limonene pathway. Following transformation of *Escherichia coli* XL-1 with a pBluescriptII SK⁻ plasmid library of BR388 chromosomal DNA and selection of transformants by growth on M9. salts agar and limonene vapor, small colonies were observed after 6 days of incubation. Following verification of growth on limonene by subsequent transfers, one transformant, designated EC409A, was selected for further characterization, and was found to contain a 9.6 kb insert which was an endonuclease EcoRI digest with the restriction map shown in FIG. 2. Hybridization experiments shown in FIG. 3 indicated a single copy of this insert in the chromosome of the BR388 thermophile parent ATCC 55596.

Figure 4:
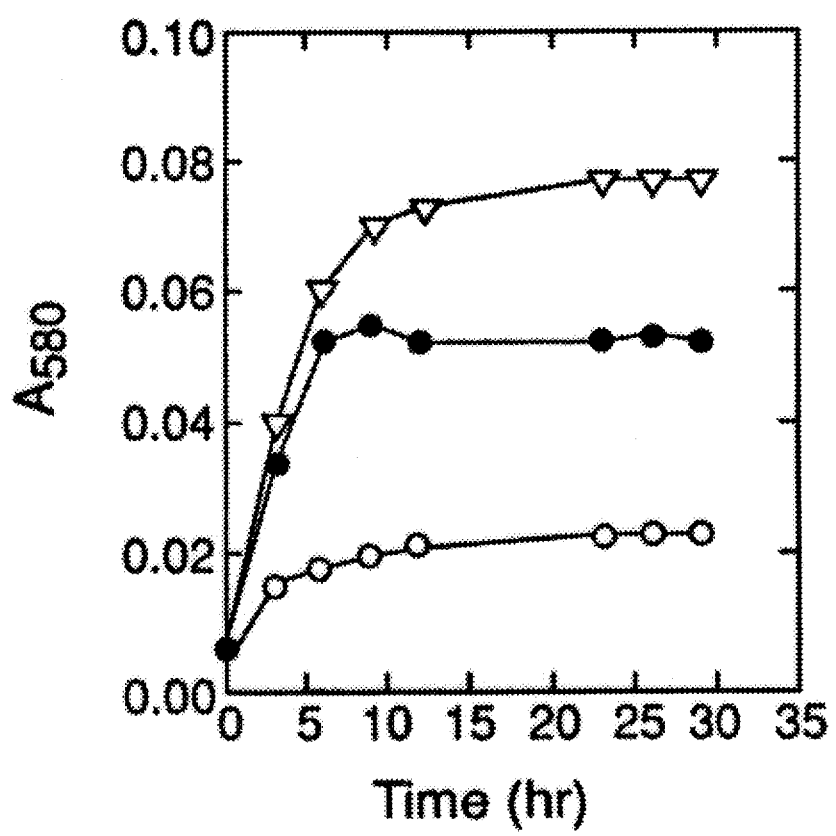
FIG. 4 shows growth of *Escherichia coli* recombinant EC409A on limonene. (O), limonene vapor alone: (●), 0.006% yeast extract alone; (△), 0.006% yeast extract and limonene vapor.

Growth studies of *E. coli* EC409A in liquid culture. Growth studies of transformant EC409A in M9 salts with limonene vapor showed that the transformant could utilize limonene vapor as a sole carbon source in liquid cultures, although biomass levels were low (FIG. 4). Addition of yeast extract at a low concentration of 0.6 mg/L was found to elevate biomass levels while retaining limonene-stimulated growth, and was used in certain of the experiments below.

Production of monoterpenes during growth on limonene. Monoterpene products produced by recombinant EC409A during growth on limonene vapor and 0.6 mg/L yeast extract and are shown in Table 1, where α-terpineol was observed as a major product, with highest production during exponential growth and decreased amounts in the stationary phase.

TABLE 1

Limonene bioconversion products of *E. coli* transformant EC409A

| Growth stage | Metabolites | Concentration (mg/L) |
| --- | --- | --- |
| early log (6h) | α-terpineol | 1.4 |
| late log (24 h) | α-terpineol | 33 |
|  | perillyl alcohol | 0.51 |
|  | perillyl aldehyde | trace |
| stationary (48h) | α-terpineol | 1.0 |

Perillyl alcohol and perillyl aldehyde were also observed during the exponential phase.

EXAMPLE 2

Growth on and bioconversion of other monoterpenes. When cells grown to exponential phase on limonene were resuspended in M9 salts with perillyl alcohol vapor, significant amounts of perillaldehyde and perillic acid were produced after 36 hours (Table 2).

TABLE 2

Bioconversion of perillyl alcohol by *E. Coli* EC409A

| Metabolite | Concentration, mg/L |
| --- | --- |
| perillyl aldehyde | 36 |
| perillic acid | 230 |
| α-terpineol | not detectable |

In separation experiments, slight but reproducible enhancement of growth on 0.6 mg/L yeast extract by perillyl alcohol vapor was observed (Table 3).

TABLE 3

Growth of *E. coli* EC409A in M9 salts and 0.6 mg/L yeast extract with 0.6 mg/L yeast extract with and without perillyl alcohol vapor.

| | w/o perillyl alcohol | | w/perillyl alcohol | |
| --- | --- | --- | --- | --- |
| Time(h) | A580 | VC × 10⁻⁶ | A580 | VC × 10⁻⁶ |
| 0 | 0.009 | 9+/−1 | 0.009 | 9+/−1 |
| 6 | 0.042 | 189+/−6 | 0.048 | 245+/−7 |
| 12 | 0.048 | 240+/−5 | 0.056 | 461+/−7 |
| 24 | 0.050 | 298+/−8 | 0.061 | 485+/−11 |
| 36 | 0.050 | 111+/−7 | 0.061 | 139+/−8 |

VC: Viable count.
Growth on α-terpineol as a sole carbon source was not observed by either EC409A or the parental thermophile (data not shown).

Examples 1 and 2 show the first cloning of a functional microbial monoterpene degradation path as shown in FIG. 1. The *B. stearothermophilus* limonene pathway is functional when introduced into *E. coli*, enabling growth on limonene as a sole carbon source. The demonstrated production of both α-terpineol and perillyl alcohol by the EC409A recombinant should help determine which of the observed metabolites contribute to cellular energy. The facile conversion of perillyl alcohol to perillyl aldehyde and perillic acid by the recombinant with accompanying growth, and the inability of α-terpineol to support growth with either wild-type thermophile or limonene-degrading recombinant suggest participation of perillyl derivatives in the growth-supporting pathway, as indicated in FIG. 1.

EXAMPLE 3

In this Example, the production of carveol and carvone from (R)-(+)-limonene using a genetically engineered *E. coli* carrying genes from *Bacillus stearothermophilus* (BR388 - ATCC 55596) is described. In Example 1 the 9.6 kb fragment codes for the pathway of limonene degradation was cloned on a bluescript vector, designated *E. coli* EC409A. No carveol production was detected.

Subcloning of limonene degrading gene:

The 9.6 kb segment of EC409A was subcloned. Plasmid DNA of *E. coli* EC409A containing 9.6 kb limonene degrading gene was extracted according to the procedure of Sambrook et al (1993). EC409A is deposited as ATCC 69817 under the Budapest Treaty. The plasmid DNA was digested using the restriction enzyme HindIII. The restriction fragments, 5.2, 3.9 and 0.5 kb were collected by electroelution device. The vector plasmid, PKK 233-2 was cleaved with HindIII enzyme and dephosphorylated. The fractionated HindIII fragments were ligated with the vector DNA, and transformed into *E. coli* DH5α. Recombinants containing 3.9 kb insert DNA, designated EC418 showed growth in minimal medium using limonene as sole carbon source.

Relative to EC409A, the recombinant EC418 efficiently produced carveol, carvone, α-terpineol, and perillyl alcohol as shown in FIG. 1. The production of carveol and carvone by the subcloned recombinant has particular commercial interest, as it is used as a mint-related flavor ingredient.

Biotransformation of Limonene to Carveol:

In this Example 3, M9 salts medium supplemented with 0.006% yeast extract was used for the growth and biotransformation of limonene. Limonene was added directly to the serum bottle containing M9 medium and inoculated with *E. coli* EC418. The bottles were capped with Teflon-coated stoppers and aluminum seal. Incubation was carried out at 37° C. in a gyratory shaking water bath. Relative growth was monitored by measurement of culture turbidity at different incubation time at 550 nm in a Gilford single beam spectrophotometer corrected for absorbance of the medium.

To identify the biotransformation products, 6 to 48 hour cultures were centrifuged at 12,000×g for 20 minutes at 4° C. The filtrate was acidified to pH 2.0 and extracted thrice with ether. The ether fraction was evaporated to 25 ml, neutralized by 5% NaOH and concentrated under nitrogen. The final residue was dissolved in ethyl acetate and analyzed by GC-MS (Department of Biochemistry, Michigan State University, East Lansing, Mich.). The GC-MS system utilized was a mass spectrometer HP 5970 equipped with gas chromatograph HP 5890 (Hewlett Packard), a mass selective detector (MSD HP 5970) and fused silica capillary column (0.25 mm I.D×30M DB-wax). Conditions used were: helium carrier gas, injection port and detector port at 240° C., column temperature from 40°–240° C. at 7° C./min. with a 2 min. initial hold time. One microliter sample was injected. Limonene bioconversion products.

The amounts of bioconversion products from (R)-(+) limonene and (S)-(−) limonene varied with culture time. GC-MS chromatograms of the neutral fraction showed the presence of perillyl alcohol, α-terpineol, carveol and carvone. Control cultures did not produce any of these metabolites. At 48 h incubation period, perillyl alcohol was identified as a major component reaching 72.3 and 51.2 mg/l using (R)-(+) and (S)-(−) limonene, respectively. α-terpineol produced at the same time was 29.4 mg/l in (R)-(+) limonene and 5.36 mg/l in (S)-(−) limonene. Carveol and carvone showed maximum product ion at 6 h incubation period with 26 mg/l using (R)-(+) limonene and 2.2 mg/l using (S)-(−) limonene as substrates. Carveol and carvone production was decreased after 24 hours of incubation.

The genus and species *Bacillus stearothermophilus* is well known to those skilled in the art and can easily be isolated from citrus. The strains selected are those that metabolize limonene. Other DNA segments can be isolated from *Bacillus stearothermophilus* other than BR388 which encode proteins which perform the same function. The recombinant *Escherichia coli* can be grown using conventional *Bacillus* growth media at a temperatures between about 30° and 60° C. to produce the monoterpenes. Thus, the present invention provides a very convenient method for producing monoterpenes.

It is intended that the foregoing description be only illustrative of the present invention and that the present invention be limited only by the hereinafter appended claims.

We claim:

1. A recombinant plasmid containing a segment of DNA of a *Bacillus stearothermophilus* which provides a bacterium with the ability to convert limonene to a monoterpene compound in a culture medium.

2. The recombinant plasmid of claim 1 wherein the segment of the DNA is an endonuclease EcoR1 digest which is 9.6 kb in length.

3. The recombinant plasmid of claim 1 wherein the segment of DNA is from the *Bacillus stearothermophilus* deposited as ATCC 55596 and which has been digested with endonuclease EcoRI.

4. A recombinant plasmid as contained in *Escherichia coli* and deposited as ATCC 69817.

5. *Escherichia coli* containing a segment of DNA of segment of DNA of *Bacillus stearothermophilus* which provides a bacterium with the ability to convert limonene to a monoterpene compound in a culture medium.

6. The *Escherichia coli* of claim 5 wherein the segment is an endonuclease EcoRI digest which is 9.6 kb in length.

7. The *Escherichia coli* of claim 5 wherein the segment of DNA is from the *Bacillus stearothermophilus* deposited as ATCC 55596 and which has been digested with endonuclease EcoRI.

8. A bacterium which is *Escherichia coli* deposited as ATCC 69817.

9. A process for producing monoterpene compounds which comprises:
   (a) providing a culture medium containing cells of *Escherichia coli* containing a segment of DNA of *Bacillus stearothermophilus* which provides a bacterium with the ability to convert limonene to a monoterpene compound; and
   (b) incubating the cells in the culture medium in the presence of the limonene to produce isolatable amounts of the monoterpene compound in the culture medium.

10. The process of claim 9 wherein the culture medium contains yeast extract.

11. The process of claim 9 wherein the limonene is introduced into the culture medium as a vapor.

12. The process of claim 9 wherein the monoterpene compound is separated from the culture medium.

13. The process of claim 12 wherein the separation is by extraction into an organic solvent which extracts the monoterpene compounds.

14. The process of claim 13 wherein the solvent is ether.

15. The process of claim 9 wherein the incubating is at a temperature between about 30° and 60° C.

16. The process of claim 9 wherein the culture medium contains yeast extract, is incubated at a temperature between about 30° and 60° C. and the limonene is added as a vapor.

17. The process of claim 16 wherein the monoterpene compound is separated from the culture medium using diethyl ether as a solvent which extracts the monoterpene compound.

18. The process of claim 9 wherein there are multiple monoterpene compounds and the monoterpene compounds are extracted together from the culture medium and are separated from each other by liquid chromatography.

19. The process of claim 18 wherein the monoterpene compounds are separated by high pressure liquid chromatography.

20. The process of claim 9 wherein the monoterpene compound is selected from the group consisting of perillyl alcohol, perillyl aldehyde and α-terpineol and mixture thereof.

21. The process of claim 9 wherein in the segment is an endonuclease EcoRI digest which is 9.6 kb in length.

22. The process of claim 9 wherein the DNA is from the *Bacillus stearothermophilus* deposited as ATCC 55596 and which has been digested with EcoRI.

23. The process of claim 9 wherein the *Escherichia coli* is deposited as ATCC 69817.

24. The process of claim 9 wherein as an additional step the *Escherichia coli* grown in the limonene is isolated and then grown with perillyl alcohol to produce perillyl aldehyde and perillic acid.

25. A process for the production of carveol which comprises:

(a) providing a culture medium containing cells of *Escherichia coli* containing a segment of DNA of *Bacillus stearothermophilus* which provides a bacterium with the ability to convert limonene to carveol and carvone in the culture medium.

26. The process of claim 25 wherein the segment of the DNA is 3.9 kb in length and is a HindIII segment of a 9.6 kb EcoRI segment of the DNA of the *Bacillus stearothermophilus*.

27. The process of claim 26 wherein the 9.6 kb EcoRI segment is in the *Bacillus stearothermophilus* deposited as ATCC 55596.

28. The process of claim 26 wherein the *Escherichia coli* is deposited as ATCC 69817.

29. An *Escherichia coli* containing a segment of DNA from *Bacillus stearothermophilus* which converts limonene to carveol and carvone.

30. The *Escherichia coli* of claim 29 wherein the segment of DNA is an endonuclease HindIII digest from the *Bacillus stearothermophilus* deposited as ATCC 55596.

31. The *Escherichia coli* of claim 29 which is deposited as ATCC 69817.

32. A recombinant plasmid containing a segment of DNA from *Bacillus stearothermophilus* which provides a bacterium with the ability to convert limonene to carveol.

33. The recombinant plasmid of claim 32 wherein the segment of DNA is an endonuclease HindIII digest from *Bacillus stearothermophilus* deposited as ATCC 55596.

34. A recombinant plasmid as contained in *Escherichia coli* deposited as ATCC 69817.

35. An isolated and purified segment of DNA which is 9.6 kb segment of endonuclease EcoRI digest of DNA of *Bacillus stearothermophilus* deposited as ATCC 55596.

36. An isolated and purified segment of DNA which is a 3.8 kb endonuclease HindIII digest of a 9.6 kb segment endonuclease EcoRI digest of DNA of *Bacillus stearothermophilus* deposited as ATCC 55596.

* * * * *

UNITED STATES PATENT AND TRADEMARK OFFICE
CERTIFICATE OF CORRECTION

PATENT NO. : 5,688,673
DATED : November 18, 1997
INVENTOR(S) : Patrick J. Oriel, Srinivasan Savithiry and Hae Choon Chang It is certified that error appears in the above-indentified patent and that said Letters Patent is hereby corrected as shown below:

Column 2, line 29, "carone" should be --carvone--.

Column 4, line 47, "Tn10)))" should be --Tn10))]--.

Column 5, line 22, "perpene" should be --terpene--.

Column 8, line 29 (Claim 2), "endonuclease EcoR1" should be --endonuclease EcoRI--.

Column 8, lines 37&38 (Claim 5), delete "segment of DNA of", second occurrence.

Signed and Sealed this

Fourteenth Day of July, 1998

Attest:

BRUCE LEHMAN

*Attesting Officer*     *Commissioner of Patents and Trademarks*